United States Patent [19]

Moissonnier

[11] Patent Number: 4,489,717
[45] Date of Patent: Dec. 25, 1984

[54] DEVICE PERMITTING THE CONTROL OF THE FLEXION OF A DEFECTIVE LIMB OF A HANDICAPPED PERSON WHICH IS FITTED WITH AN ORTHOPAEDIC APPLIANCE FOR ITS SUPPORT AND ARTICULATION

[75] Inventor: Gérard Moissonnier, Le Coteau, France

[73] Assignee: Pierre Bonnabaud Sarl, Le Coteau, France

[21] Appl. No.: 396,114

[22] Filed: Jul. 7, 1982

[30] Foreign Application Priority Data

Jul. 20, 1981 [FR] France ............................. 81 14224

[51] Int. Cl.³ .............................................. A61F 1/04
[52] U.S. Cl. ......................................... 128/80 F; 3/28
[58] Field of Search ............... 128/80 R, 80 F, 87 R, 128/88; 3/28, 26, 29, 27

[56] References Cited

U.S. PATENT DOCUMENTS

| 744,801 | 11/1903 | Rowley | 3/28 |
| 792,711 | 6/1905 | Koeber | 3/28 |
| 2,513,134 | 6/1950 | Barghausen | 3/28 |
| 2,542,567 | 2/1951 | Peters | 3/28 |
| 2,559,446 | 7/1951 | Lucas et al. | 3/28 |

FOREIGN PATENT DOCUMENTS 1284563 12/1968 Fed. Rep. of Germany .
495281 11/1938 United Kingdom .

*Primary Examiner*—John D. Yasko
*Attorney, Agent, or Firm*—Parkhurst & Oliff

[57] ABSTRACT

Device permitting the control of the flexion of a defective limb of a handicapped person which is fitted with an orthopaedic appliance consisting of two rigid members (21,22) connected together by a pivot pin (26).

This device (20), situated on and as an extension of the pivot pin (26), comprises a freewheel system (12) on which a hub (10) is mounted by a force fit. A braking system composed of two articulated jaws (4,6) surrounds the hub (10).

6 Claims, 4 Drawing Figures

DEVICE PERMITTING THE CONTROL OF THE FLEXION OF A DEFECTIVE LIMB OF A HANDICAPPED PERSON WHICH IS FITTED WITH AN ORTHOPAEDIC APPLIANCE FOR ITS SUPPORT AND ARTICULATION

The present invention relates to an improved device intended to be fitted to orthopaedic appliances used for the support and articulation of a defective limb with an arthrodial joint of a handicapped person, for example a person suffering from monoplegia of the lower limbs.

In the remainder of the description the invention will be described in connection with an orthopaedic appliance intended to be associated with a lower limb having an arthrodial joint (leg), but it is obvious that this is not limitative and that the appliance according to the invention could also be fitted to orthopaedic appliances used for palliating deficiencies in the upper limbs, for example in the case of paralysis of the triceps.

Orthopaedic appliances used for palliating the deficiencies of a limb of a handicapped person are currently referred to as "ortheses" in order to differentiate them from prostheses, which are appliances intended to replace an amputated limb. Although the expression "orthesis" is not in current use in ordinary language, for the sake of simplification it will be adopted in the remainder of the description given below.

Ortheses are orthopaedic appliances which make it possible to provide support and articulation for a defective limb of a handicapped person. When they are associated with a leg, appliances of this kind are essentially composed of two rigid members connected together by a pivot pin, one of these members being immobilized against the thigh and the other against the calf, for example by means of bracelets. The pivot pin connecting these two rigid members together is disposed at the knee articulation.

The problem arising with the ortheses generally used up to the present time consists in that they do not make it possible to brake the flexion of the paralyzed limb when the body is supported on the limb in question. Consequently, rapid and jerky movements take place, which are difficult to control and may entail a loss of balance. Moreover, since the movements are not braked at the axis of the knee, this entails pronounced limping due to the necessary flexion of the other leg, which may result in a fall if the extension and then the locking are not effected correctly. Furthermore, as a step is due to a contraction of the lumbar cone, its repetition gives rise to considerable pain in the lumbar region, with muscular contracture and deviation of the vertebral column (scoliosis, tilting of the pelvis).

The devices used as prostheses, that is to say appliances serving to replace amputated limbs, and which incorporate braking systems, unfortunately cannot be fitted to ortheses in view of the fact that in this case the limb still exists.

It is true that it has been proposed, particularly in German Pat. No. 1,284,563, to control the flexion of the limb by providing the orthesis with a disc brake system. Unfortunately, a system of this kind is particularly complex and cannot be fitted to existing ortheses.

A simple, improved device, constituting the subject of the present invention, has now been found which makes it possible to control the flexion of a defective limb with an arthrodial joint of a handicapped person which is fitted with an orthopaedic appliance of the orthesis type enabling the problems mentioned above to be solved. Furthermore, the device according to the invention can, without any particular difficulty, be fitted to existing ortheses.

Not only does a device of this kind make it possible to brake the flexion of the paralyzed limb, for example of the leg when the body is supported on it during normal walking, but it also permits the free extension of the said limb. In addition, the appliance according to the invention is of very small dimensions, can be made of light metal, and causes no discomfort during its use. Since it is small in size, it can easily be hidden.

Generally speaking, therefore, the invention relates to a device which permits control of the flexion of a defective limb of a handicapped person which is fitted with an orthopaedic appliance consisting of two rigid members connected together by a pivot pin, each member being removably fixed to one of the parts of the defective limb.

The appliance according to the invention is characterized in that it comprises:

On the one hand, fixed on and as an extension of the pivot pin, a freewheel system on which a hub is mounted by a force fit, the said freewheel
(a) being self-locking in flexion, thus avoiding the collapse of the leg, and
(b) ineffective and therefore free in the extension movement, thus enabling the limb and the orthesis to resume through inertia the position of support;

on the other hand a braking system composed of two articulated jaws provided with shoes surrounding the hub, the said jaws being mounted for pivoting on a pin fastened to the upper rigid member of the orthesis and being associated with a system of adjustment of the pressure of the shoes on the hub.

Furthermore, the device according to the invention is associated with a system making it possible to adjust the pressure of the jaws on the hub, and in addition, the brake shoes are preferably mounted in cages enabling them to be easily changed.

Not only can an appliance of this kind easily be mounted on ortheses associated with a leg, but it can, if desired, be associated with ortheses used for the upper limbs.

The invention and the advantages which it provides will however be better understood with the aid of the example of embodiment given below by way of indication but without constituting a limitation, this example being illustrated by the accompanying drawings, in which.

Figure 1:
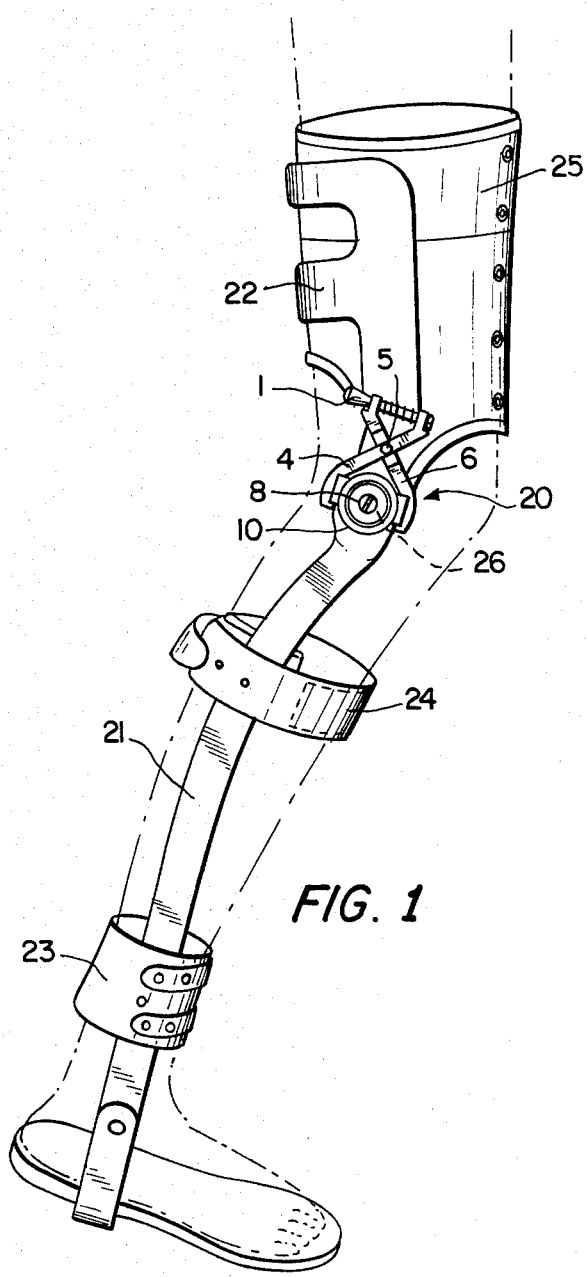
FIG. 1 shows diagrammatically in perspective a leg ortheses equipped with a device according to the invention.

Referring to the accompanying drawings, the device according to the invention, which is given the general reference (20) in FIG. 1 and which makes it possible to control the flexion of a defective limb (leg) of a handicapped person, is associated with the orthopaedic apparatus ensuring the support and flexion of the leg, this orthopaedic apparatus being known as an "orthesis" and being composed of two rigid members (21, 22) connected together by a pivot pin (26) situated substantially at knee level. Each member (21,22) is removably fixed, around the thigh in the case of one (22) of them and along the calf in the case of the other (21). This whole arrangement is fastened by means of adjustable bracelets (23, 24, 25) around the leg shown in dashed lines in FIG. 1.

Figure 2:
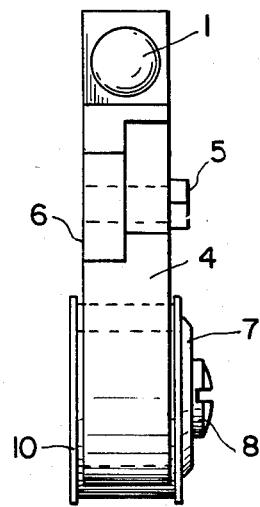
FIGS. 2 and 3 are respectively front and side views of a device according to the invention.
Figure 3:
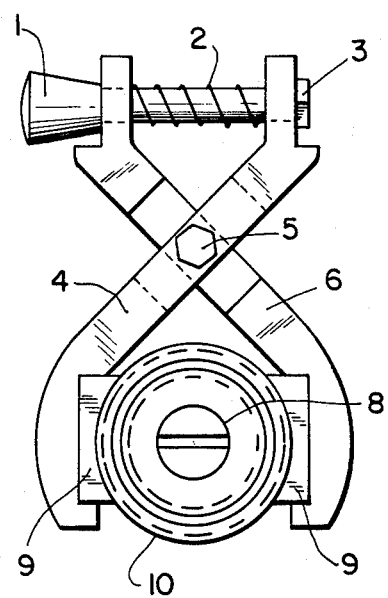
Figure 4:
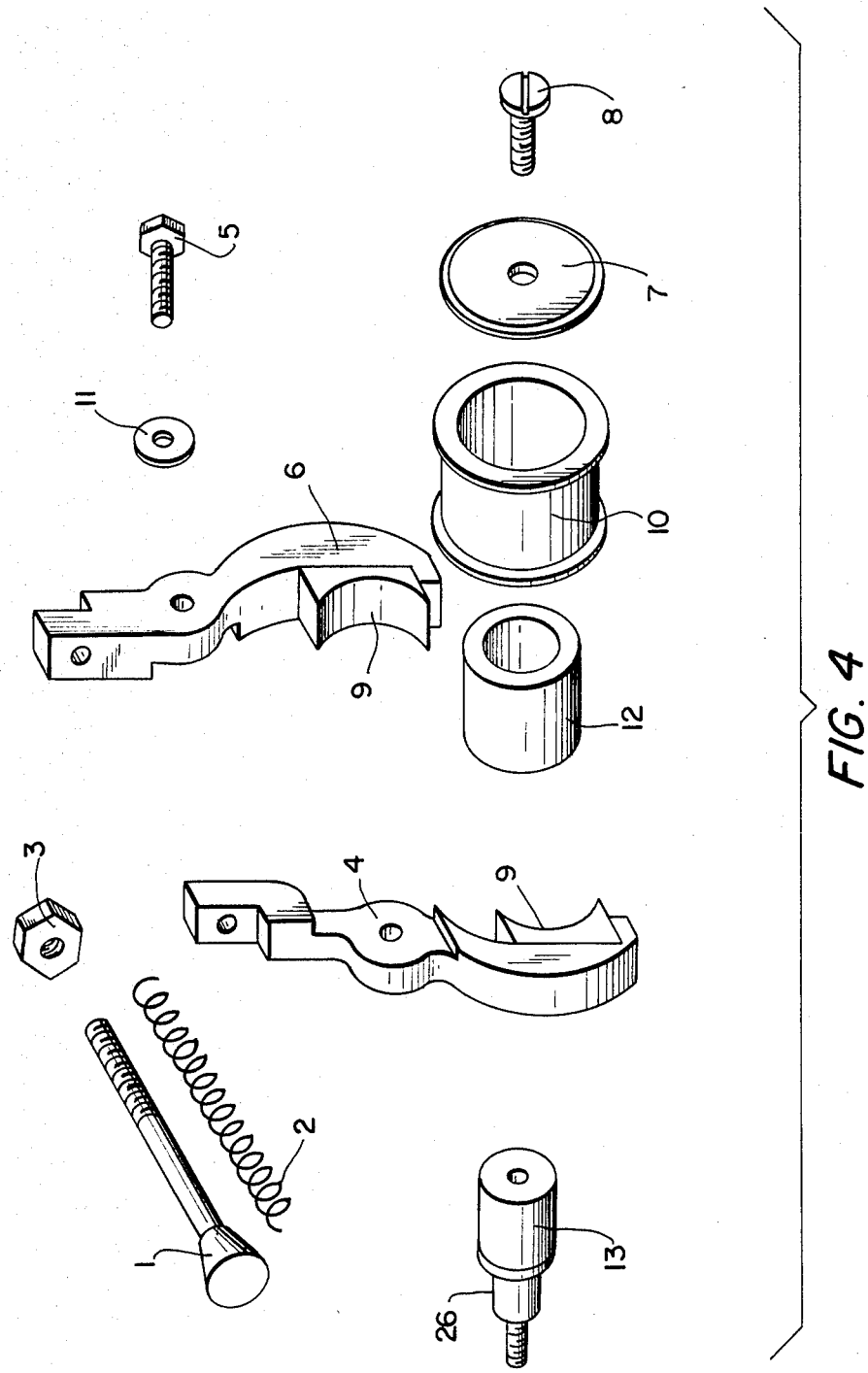
FIG. 4 is an exploded view showing in detail all the parts of which a device of this kind is composed.

The device according to the invention, as can clearly be seen in FIGS. 2, 3, and 4, is composed of the following elements:

Firstly, fixed on and as an extension of the pivot pin (26) connecting the two rigid members (21,22,) is mounted a freewheel system (12) of known type, for example a freewheel marketed by the INA Company under the reference HF 1616. This freewheel is mounted on a turned and ground shaft (13) extending the pivot pin (26) of the two parts of the orthesis. The freewheel (12) is inserted as a force fit in a hub (10), for example of duraluminium, which is closed at the end, on the outer side, by a cap (7), which is for example of steel and which in turn serves as a side stop and is held in place by a screw (8). The said freewheel (12) is self-locking in flexion and thus prevents the collapse of the leg, and in addition is ineffective and therefore free in the extension movement thus enabling the limb and the orthesis to resume through inertia the position of support.

Furthermore, the device according to the invention also contains a braking system composed of two symmetrical, articulated jaws (4, 6) supporting shoes (9), which bear against the periphery of the hub (10) fastened to the pivot pin (26) of the orthesis. These two jaws are mounted for pivoting on a pin (5) provided on the upper part (22) of the orthesis. In addition, these jaws are associated with a system of adjustment of the pressure of the shoes (9) on the hub (10), this adjustment system being composed of a threaded screw (1) provided with a compensating spring (2) and a nut (3). This arrangement makes it possible to control the locking or unlocking of the two jaws (4) and (6). The braking action is due to the pressure of the jaws (4) and (6) on the hub (10), this pressure being controlled by the adjustment screw (1), which is provided with a knurled knob permitting its operation. The adjustment screw (1) passes through the two upper branches of the jaws, in which two apertures are provided for the purpose, and is screwed into the nut (3) corresponding to it in diameter. The compression spring (2) surrounding the screw acts as compensator. The central portion of the jaws is pivoted on a threaded pin (5), with the optional use of spacer washers (11). In the bottom portion of each branch are disposed machined shoes (9), for example of rubber. Any other type of material, such as bakelised felt or "ferrodo", could be course also be used. The shoes are preferably inserted into sockets provided in the curved bottom portion of the jaws (4,6,) and are held in place by the pressure applied to the hub (10). An arrangement of this kind enables the shoes (9) to be changed easily.

With the aid of a device of this kind, which is fixed externally on the pivot (26) of the orthesis, at knee level, and which may be of light metal, it is possible to control effectively the flexion of the defective limb, without entailing any discomfort or handicap for the user. Moreover, a device of this kind, being of small dimensions, can easily be hidden.

The device functions in the following manner.

The two jaws (4,6,) the tightness of which can be adjusted, and which are provided with shoes (9), apply pressure and brake the hub (10), inside which the freewheel (12) is situated. The jaws are fixed on the upper portion of the orthesis, on the pin (5), while the hub (10) and the freewheel (12) are mounted on the actual pivot pin (26) of the joint by means of the shaft (13) extending the said pivot pin.

Consequently, in flexion, the freewheel (12) being locked, the jaws (4,6) act as a brake on the hub (10) itself, thus preventing the abrupt collapse of the leg and consequently making it impossible for the user to fall.

In extension, the weight of the limb and of the orthesis has the effect that when the arrangement is brought by inertia into the position of support, the freewheel (12) is released.

An appliance of this kind, which can be fitted on both sides of any kind of orthesis, thus solves the problem of controlling the flexion of the limb during walking. It therefore practically completely eliminates fatigue of the user, and the unbalancing of the pelvis. Finally, psychologically, the use of an appliance of this kind gives the user a feeling of safety.

This type of appliance can be mounted on any existing ortheses in which flexion requires effort and control. This appliance can obviously be fitted not only to ortheses used for the lower limbs, but also in cases of deficiency of the upper limbs and, in addition to monoplegia due to reactions of a neurological type, it could also be applied in cases of deficiency of the poliomielytic type.

I claim:

1. An orthopedic appliance for fitting a defective limb of a handicapped person which limb comprises two limb members connected by a substantially arthrodial joint comprising:
    a first rigid member attachable to a first of the two limb members;
    a second rigid member attachable to a second of the two limb members;
    said first and second rigid members pivotally connected together by a pin with means for flexion about the axis of said arthodial joint;
    a self-locking freewheel system mounted on a shaft extension of said pivot pin with said self-locking freewheel system having means for self-locking in flexion to prevent the collapse of the limb and means for allowing free extension and movement of said limb through inertia to resume a position wherein said appliance supports said limb;
    said self-locking freewheel system comprising a freewheel and a hub which is force fit over said freewheel
    a braking mechanism with means for acting on said hub of said self-locking freewheel system thereby preventing abrupt collapse of the limb;
    means for adjusting the amount of braking performed by said braking mechanism.

2. An appliance as claimed in claim 1 wherein said braking mechanism comprises:
    articulated jaws provided with shoes;
    said shoes disposed about said hub;
    said jaws mounted for pivoting on a pin fastened to said appliance and associated with said means for adjusting the amount of braking, which adjusts the pressure of said shoes on said hub.

3. An appliance as claimed in claim 2 wherein said means for adjusting the amount of braking comprises:
    a threaded screw, and
    compression spring holding means for maintaining the position of said screw.

4. An appliance as claimed in claim 2 wherein said shoes are mounted in cages disposed on said jaws.

5. An appliance as claimed in claim 1 adapted to fit a leg of a handicapped person and attachable to the leg above and below the knee.

6. An orthopedic appliance as claimed in claim 1 wherein said hub further comprises a cap with means for attaching said cap to one side of said hub.

* * * * *